United States Patent [19]

Kramm et al.

[11] 4,204,010

[45] May 20, 1980

[54] RADIATION CURABLE, ETHYLENICALLY UNSATURATED THIXOTROPIC AGENT AND METHOD OF PREPARATION

[75] Inventors: David E. Kramm, Laurel; Arthur D. Ketley, Columbia, both of Md.

[73] Assignee: W. R. Grace & Co., New York, N.Y.

[21] Appl. No.: 972,127

[22] Filed: Dec. 21, 1978

Related U.S. Application Data

[63] Continuation-in-part of Ser. No. 855,072, Nov. 25, 1977, abandoned, which is a continuation-in-part of Ser. No. 724,196, Sep. 17, 1976, abandoned.

[51] Int. Cl.$^2$ .............................................. B05D 3/06
[52] U.S. Cl. ................................. 427/44; 204/159.22; 260/404.5; 260/18 TN; 560/26; 560/158; 427/54.1
[58] Field of Search ............ 260/404.5, 468 E, 471 C, 260/452 B, 18 TN; 560/26, 158; 427/DIG. 5, 44, 54; 204/159.22

[56] References Cited

U.S. PATENT DOCUMENTS

| | | | |
|---|---|---|---|
| 3,183,109 | 5/1965 | Neumann et al. | 260/18 TN |
| 3,781,214 | 12/1973 | Nemoto et al. | 260/18 TN |
| 3,898,349 | 8/1975 | Kehr et al. | 427/44 |
| 3,979,426 | 9/1976 | DeMajistre | 520/26 |
| 3,991,024 | 11/1976 | Nakamoto et al. | 260/18 TN |

*Primary Examiner*—John H. Newsome
*Attorney, Agent, or Firm*—Richard P. Plunkett; Edward J. Cabic

[57] ABSTRACT

This invention relates to an ethylenically unsaturated reactive thixotropic agent for use in radiation curable compositions, e.g., overprint varnishes, formed by reacting a hydroxyl-containing fatty acid ester with an ethylenically unsaturated isocyanate. The agent not only performs its thixotropic function in the uncured state but also forms part of the cured product on exposure to radiation, e.g., UV radiation due to its substantially similar reactivity.

10 Claims, No Drawings

RADIATION CURABLE, ETHYLENICALLY UNSATURATED THIXOTROPIC AGENT AND METHOD OF PREPARATION

This application is a continuation-in-part of copending application Ser. No. 855,072, filed Nov. 25, 1977, now abandoned, which, in turn, is a continuation-in-part of application having Ser. No. 724,196, filed Sept. 17, 1976, and now abandoned.

This invention relates to reactive thixotropic agents. More particularly, this invention relates to ethylenically unsaturated reactive thixotropic agents for use in radiation curable compositions.

Thixotropic agents are used in many applications, especially in the coating field to obtain the desired viscosity of the material so that it can be applied in the desired manner. However, present day thixotropic agents have many drawbacks. For instance, many thixotropic agents are inorganic and, when admixed with organic coating compositions, exhibit a non-homogeneity in blending and also have a tendency to exude from the composition after it has been applied. This is especially true in radiation curable compositions. Even organic thixotropic agents which are not reactive on exposure to radiation fail to yield good coatings since the uncured thixotropic agent causes a reduction in gloss in the final coating. Additionally, thixotropic agents which are not reactive on exposure to radiation are the cause of an incomplete cure, especially in lines which run at speeds up to 800 ft per minute. Coatings which are incompletely cured are hazy and they scratch easily. Another drawback is that incompletely cured coatings when stacked cause blocking.

One object of the instant invention is to produce a reactive thixotropic agent. Another object of the instant invention is to produce an ethylenically unsaturated reactive thixotropic agent which is cured into the product on exposure to radiation. Yet another object of the instant invention is to set forth a method of making an ethylenically unsaturated reactive thixotropic agent. Still another object of the invention is to produce an ethylenically unsaturated reactive thixotropic agent the unsaturation in which is of similar reactivity to that of the radiation curable material to which it is added so that it readily and simultaneously forms part of the cured product on exposure to radiation.

Another object of the invention is to produce a varnish, containing said ethylenically unsaturated reactive thixotropic agent, which when applied over either wet conventional or radiation curable inks will form a coherent, continuous film, thus "trapping" the ink so that when the varnish is cured by radiation the inks will be covered by a smooth, glossy coating. It is of particular advantage if such varnish application can be conducted on the same multi-unit press as is used for printing down the inks, since the user may then carry out both the printing and varnishing steps in one operation. Application of conventional solvent based varnishes cannot be conducted on press due to relatively long drying times so that printing and varnishing have, in this case, to be conducted in two separate operations.

Varnishes containing the thixotropic agents of this invention can be applied from either the inking or dampening units of printing presses or by other means to any printed surface where gloss and abrasion resistance are required—for example, cartons, magazine covers, tags and labels.

Coatings that are applied through the "form" or inking rolls of a press are commonly referred to as varnishes. The term "lacquer" is frequently used for similar materials if they are applied through the dampening system of the press or off-line with a roller-coater. As used herein the term "coating" includes both U.V. curable varnishes and lacquers. As used herein the term "paper product" includes paper and paperboard, coated or uncoated, which may have printed on its surface designs, text, etc., all of which are receptive to the varnishes and lacquers containing the thixotropic agent of the instant invention.

The ethylenically unsaturated reactive thixotropic agent of the instant invention has the general formula:

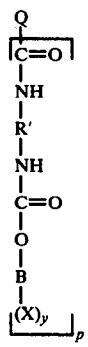

wherein
Q is the residue obtained by removal of H from primary OH groups of the reaction product from the esterification of a polyhydric alcohol containing primary OH groups with only a fatty carboxylic acid containing 4 to 26 carbon atoms in a saturated aliphatic hydrocarbon chain;
R' is an aliphatic or aromatic polyvalent organic moiety of a polyisocyanate after reaction of the isocyanato groups,
B is an aliphatic hydrocarbon containing 1–36 carbon atoms,
X is a member of the group consisting of

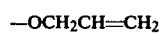

and

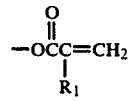

wherein $R_1$ is hydrogen or a methyl group, and p and y are each integers from 1–10.

The thixotropic agent of the instant invention is formed by reacting a primary hydroxyl-containing fatty acid ester with an unsaturated isocyanate containing terminal unsaturation. Preferred unsaturation is of the allylic, acrylic or methacrylic type since it is necessary that the thixotropic agent reacts under radiation with the radiation curable material at a rate similar to that at which the latter cures. Thus it is critical that the thixotropic agent contain terminal ethylenic unsaturation. Slowly curing materials, such as those containing internal unsaturation, are not suitable for this application since they cure at rates requiring a hundred-fold or more excess in time thereby precluding their commercial acceptability in conjunction with radiation curable material. The reaction is preferably carried out at temperatures in the range 40°-80° C. using well-known conventional urethane catalysts such as stannous octoate, stannous oleate, dibutyltin dilaurate, and the like. Higher temperatures up to 150° C. are sometimes employed in the event the catalyst is omitted.

The ethylenically unsaturated reactive thixotropic agent of the instant invention is present in the radiation curable compositions in amounts ranging from about 5-15 weight percent of the composition. Greater amounts are operable but unnecessary.

The preferred hydroxy-containing fatty acid esters have primary hydroxyl groups. These OH groups react very readily as compared with secondary OH with the NCO groups of the isocyanate ensuring no residual trace NCO remains in the product. Furthermore, the reaction rate is such that the thixotropic agent can be formed at the same time in the same reactor as an acrylated urethane oligomer which forms a major component of the varnish. To form this primary hydroxyl-containing acid ester employed in the instant invention, either of the following methods are operable: A polyhydric alcohol (polyol) and a fatty carboxylic acid containing 4-26 carbon atoms are reacted in a conventional esterification reaction using an acid catalyst such as p-toluene sulfonic acid, in a solvent, e.g., benzene, toluene, xylene, dichloroethane and the like or the di, tri, tetra, etc., ester of a polyhydric alcohol and a fatty acid can be partially hydrolyzed.

Polyhydric alcohols (polyols) operable herein include, but are not limited to, styrene-allyl alcohol copolymers, hydroxy-terminated polymers based on epsilon caprolactone or analogs thereof, ethylene glycol, propylene glycol, butylene glycol, dipropylene triethylene glycol, neopentyl glycol, trimethylene glycol, polyethylene glycol, polypropylene glycol, 1,5-pentanediol, trimethylolethane, trimethylolpropane, glycerol, 1,2,6-hexanetriol, pentaerythritol, 2,2-bis(hydroxyethoxyphenyl) propane, 2,2-bis(beta-hydroxypropoxyphenyl)propane, 2,2-dimethyl-1,3-propanediol, 2,2-diethyl-1,3-propanediol, 3-methyl-1,5-pentanediol, N-methyl and N-ethyldiethanolamines. Others include 4,4'-methylenebiscyclohexanol, 4,4'-isopropylidenebiscyclohexanol and various xylenediols, hydroxymethyl phenethyl alcohols, hydroxymethylphenylpropanols, phenylenediethanols, phenylene-dipropanols, NN'-bis (2-hydroxyethyl) dimethylhydantoin, cyclohexanedimethanol, ethoxilatedbisphenol A, tris-hydroxyethyl isocyanurate, phenyldiethanolamine, trimethylolpropane, and the like.

The fatty carboxylic acids operable herein to form the hydroxy-containing fatty acid esters are well known to those skilled in the art and include such acids as butyric, isovaleric, caproic, caprylic, capric, lauric, myristic, palmitic, stearic, arachidic, behenic, ligoceric, cerotic, Δ9-decylenic, stillingic, Δ9-dodecylenic, palmitoleic oleic, ricinoleic, petroselinic, vaccenic, linoleic, linolenic, elcostearic, licanic, parinaric, gadoleic, arachidonic, cetoleic, erucic, selacholeic, nervonic.

The fatty acid esters that may be partially hydrolyzed to give the thixotropic agents of the present invention are those formed from any of the above fatty acids and the alcohols listed plus alcohols such as glycerin, sorbitol, mannitol, etc., having secondary hydroxyl groups.

In forming the ethylenically unsaturated isocyanate, polyisocyanates of the general formula $R'(NCO)_x$ wherein $R'$ is an aliphatic or aromatic polyvalent organic moiety and $x$ is at least 2 are employed. Operable polyisocyanates include but are not limited to 2,4-tolylene diisocyanate, 2,6-tolylene diisocyanate, 4,4'-diphenylurethane diisocyanate, dianisidine diisocyanate, tolidine diisocyanate, hexamethylene diisocyanate, the m- and p-xylylene diisocyanates, tetramethylene diisocyanate, 4,4'-methylene bis(cyclohexyl) isocyanate, cyclohexane-1,4-diisocyanate diphenyl ether, 2,4,6-triisocyanate toluene, 4,4',4"-triisocyanate triphenyl methane, diphenylene-4,4-diisocyanate, 1,5-naphthalene diisocyanate, cumene-2,4,6-diisocyanate, 4-methoxy-1,3-phenylene diisocyanate, 4-chloro-1,3-phenylene diisocyanate, 4-bromo-1,3-phenylene diisocyanate, 4-ethoxy-1,3-phenylene diisocyanate, 2,4'-diisocyanate diphenyl ether, 5,6-dimethyl-1,3-phenylene diisocyanate, 2,4-dimethyl-1,3-phenylene diisocyanate, 4,4-diisocyanate diphenyl ether, benzidine diisocyanate, 4,6-dimethyl-1,3-phenylene diisocyanate, 9,10-anthracene diisocyanate, 4,4'-diisocyanato dibenzyl, 3,3'-dimethyl-4,4'-diisocyanato diphenyl, 2,4-diisocyanatostilbene, 3,3'-dimethyl-4,4'-diisocyanato phenyl methane, 3,3'-dimethoxy-4,4'-diisocyanato diphenyl, 1,4-anthracene diisocyanate, 2,5-fluorene diisocyanate, 1,8-naphthalene diisocyanate, 2,6-diisocyanato benzfuran, amyl benzene-2,4-diisocyanate, hexyl benzene-2,4-diisocyanate, dodecyl benzene-2,4-diisocyanate, butyl benzene-2,4-diisocyanate, polymethylene diisocyanates, such as tretramethylene diisocyanate pentamethylene diisocyanate hexamethylene diisocyanate, cycloalkylene diisocyanates, such as cyclohexylene-1,4- diisocyanate, adducts of polyalcohols and diisocyanates which have at least 2 free isocyanate groups, e.g. adducts of trimethyolpropane and 3 moles of toluene diisocyanate, and the like.

The polyisocyanates are reacted with unsaturated alcohols in an amount that only one NCO group on the polyisocyanate remains after the reaction is complete. This remaining NCO group is thereafter reacted with a hydroxyl group on the hydroxyl-containing, fatty acid ester to form the thixotropic agent of the instant invention.

The urethane forming reaction of the polyisocyanate with an unsaturated alcohol is carried out at a temperature in the range 50°-100° C., preferably using a conventional urethane forming catalyst such as stannous octoate, stannous oleate, dibutyl tin dilaurate etc., in the absence of a solvent. In the event that one of the reactants is a solid, conventional solvent, e.g. toluene, benzene xylene, dichloroethane, and the like, can be employed. The exothermic reaction is usually continued for about 1-6 hrs. after the exotherm is complete.

Illustrative of the operable reactive unsaturated alcohols which may react with the polyisocyanates to give the desired eneisocyanate include but are not limited to allyl and methallyl alcohol, crotyl alcohol, ω-undecylenyl alcohol, 2-vinyloxyethanol, vinylhydroxyethyl sulfide, propargyl alcohol, 1-allylcyclopentanol, 2-methyl-3-butene-2-ol. Reactive unsaturated derivatives of polyhydric alcohols such as glycols, triols, tretraols, etc., are also suitable. Representative examples include trimethylolpropane or trimethylolethane diallyl ether, pentaerythritol triallyl ether, and the like. Mixtures of various reactive unsaturated alcohols are operable as well. Reactive unsaturated alcohols can also be represented by hydroxyalkyl acrylyl compounds and can be illustrated by hydroxyethyl acrylate, hydroxyethyl methacrylate, hydroxypropyl acrylate, hydroxypentyl methacrylate, and the like.

A suitable ethylenically unsaturated isocyanate is prepared by treating one mole of trimethylbenzene triisocyanate with two moles of trimethylolpropane diallyl ether. The resulting urethane containing ene-isocyanate is a polyene having four reactive allyl ether groups per molecule. Mixtures of various ene-or yne-isocyanates are operable as well.

Another operable ethylenically unsaturated isocyanate used as a reactant to form the thixotropic agent of the instant invention is that formed by reacting one mole of toluene diisocyanate with one mole of hydroxypropyl acrylate. The thus formed ethylenically unsaturated isocyanate is thereafter reacted with a hydroxyl containing fatty acid ester, e.g. glycerol monostearate to form a thixotropic agent of the instant invention.

The thixotropic agent of the instant invention imparts thixotropic properties to liquid radiation curable vehicles which are used as varnishes, coatings, photoresist adhesives, sealants, and the like. The liquid, radiation curable vehicles or composition contain at least one component which is ethylenically unsaturated and which, on exposure to radiation, homopolymerizes or, in the event it contains more than one ethylenically unsaturated component, copolymerizes. Another radiation curable system with which the thixotropic agents herein are operable is that containing an ethylenically unsaturated component and a crosslinking agent, e.g. a polyene and a polythiol which on exposure to radiation results in a cured polythioether product. An example of this system is set out in U.S. Pat. No. 3,898,349 and 3,661,744, both incorporated herein by reference. Due to the ethylenic unsaturation in the thixotropic agent, it copolymerizes or cures into the system on exposure to radiation.

Although the preferred means of curing is by means of electromagnetic radiation of wavelength of about 2000–7000 A (because of simplicity, economy and convenience), the liquid composition containing the ethylenically unsaturated thixotropic agent of the instant invention can be cured also by high energy ionizing irradiation. A preferred feature of the ionizing irradiation operation of the instant invention is treatment with high energy particle irradiation or by gamma-rays or X-rays. Irradiation employing particles in the instant invention includes the use of positive ions (e.g. protons, alpha particles, and deuterons, and also electrons or neutrons). The charged particles may be accelerated to high speeds by means of various voltage gradient mechanisms such as a Van de Graaff generator, a cyclotron, a Cockroft Walton accelerator, a resonant cavity accelerator, a betatron, a G.E. resonant transformer, a synchrotron or the like. Furthermore, particle irradiation may also be supplied from cathodic ray tubes, radioactive isotopes or an atomic pile. Gamma rays or X-rays may be obtained from radio isotopes (e.g. cobalt 60) or by particle bombardment of suitable target).

The preferred radiation for the curing reaction is actinic radiation, suitably in the wavelength of about 2000 to 7000 A, preferably for 2000 to 4000 A.

A class of actinic light useful herein is ultraviolet light, and other forms of actinic radiation which are normally found in radiation emitted from the sun or from artificial sources such as Type RS Sunlamps, carbon arc lamps, xenon are lamps, mercury vapor lamps, tungsten halide lamps, and the like. Ultraviolet radiation may be used most efficiently if the photocurable or photopolymerizable composition contains a suitable photosensitizer. Curing periods may be adjusted to be very short and hence commercially economical by proper choice of ultraviolet source, photosensitizer and concentration thereof, temperature and molecular weight, and reactive group functionality. Curing periods of less than about 1 second duration are possible, especially in thin film applications such as desired, for example, in coatings, adhesives and photoimaged surfaces.

Useful ultraviolet (U.V.) radiation has a wavelength in the range of about 2000 to 4000 Angstrom units. When ultraviolet radiation is used for the curing reaction, a dose of 0.0004–6.0 watts/cm$^2$ is usually employed. If high energy ionizing irradiation is used, e.g. electron beam, a dose in the range of 0.01–10 megarads is employed at a dose rate of $1.0 \times 10^4$–4000 megarads/second. Any radiation having an energy of greater than 3.0 electron volts is operable to cause the curing reaction of the instant invention.

Various photosensitizers are operable and well known to those skilled in the art. Examples of photosensitizers used in connection with actinic radiation include, but are not limited to, benzophenone o-methoxybenzophenone, acetophenone, o-methoxyacetophenone, acenaphthene-quinone, methyl ethyl ketone, valerophenone, hexanophenone. γ-phenylbutyrophenone, p-morpholinopropiophenone, dibenzosuberone, 4-morpholinobenzophenone, benzoin, benzoin methyl ether, 4'-morpholinodeoxybenzoin, p-diacetylbenzene, 4-aminobenzophenone, 4'-methoxyacetophenone, benzaldehyde, o-methoxybenzaldehyde, α-tetralone, 9-acetylphenanthrene, 2-acetylphenanthrene, 10-thioxanthenone, 3-acetylphenanthrene, 3-acetylindole, 9-fluorenone, 1-indamone, 1,3,5-triacetylbenzene, thioxanthen-9-one, xanthene-9-one, 7-H-benz[d]anthracen-7-one, 1 naphthaldehyde, 4,4'-bis(dimethylamino)-benzophenone, fluorene-9-one, 1'-acetonaphthone, 2'-acetonaphthone, triphenylphosphine, tri-O-tolylphosphine, acetonaphthone and 2,2-butanedione, benz[a]anthracene 7,12 dione, 2,2-dimethoxy-2-phenylacetophenone, 2,2-diethoxyacetophenone, etc., which serve to give greatly reduced exposure times and thereby when used in conjunction with various forms of energetic radiation yield very rapid, commercially practical time cycles by the practice of the instant invention.

These photosensitizers may range from about 0.005 to 50 percent by weight of the photocurable or photopolymerizable composition, preferably 0.05 to 25 percent.

The following examples are set down to illustrate, but expressly not limit, the instant invention. Unless otherwise noted, all parts and percentages are by weight.

EXAMPLE 1

253 g. of commercially available trimethylolpropane diallyl ether (4.54 meq. OH/g.) was added dropwise to a 3 neck flask containing 200 g of toluene diisocyanate (an 80/20 mixture of the 2,4 and 2,6 isomers) (11.48 meq. NCO/g.). The reaction was continued with stirring at 60° C. for 8 hours at which time the product had an NCO content of 2.42 meq./g.

To a separate 3 neck resin kettle was charged 109.5 g. of glycerol monostearate (4.42 meq. OH/g.), commercially available from Glycol Chemicals Inc. under the tradename "ALDO MSLG". This material (m. pt. 57°–61° C.) was melted. To this material were added 0.15 g. of stannous octoate and dropwise 200 g. of the reaction product of toluene diisocyanate and trimethylol propane diallyl ether supra. After the addition was complete, the temperature was held at 60°–65° C. until NCO was zero as determined by IR. On cooling, a cream colored solid (309.5 g.) resulted with 3.40 mmoles unsaturation/g. and 0.05 meq. OH/g. and will be referred to hereinafter as thixotropic agent G.

EXAMPLE 2

253 g. of commercially available trimethylolpropane diallyl ether (4.54 meq. OH/g.) was added dropwise to a 3 neck flask containing 200 g. of toluene diisocyanate (an 80/20 mixture of the 2,4 and 2,6 isomers) (11.48 meq. NCO/g.). The reaction was continued with stirring at 60° C. for 8 hours at which time the product had an NCO content of 2.42 meq./g.

To the above heated 60° C. was charged dropwise 197.9 g. of ethylene glycol monostearate (1.99 meq. OH/g.), commercially available from Glycol Chemicals Inc. under the tradename "PEGOSPERSE 50 MS" having a melting point of 56.61° C. along with 0.38 g. of stannous octoate catalyst. After addition of the ethylene glycol monostearate the NCO content remained high requiring the temperature to be raised to 80°–90° C. and the addition of 2 drops of stannous octoate. An additional 10 g. of ethylene glycol monostearate was added dropwise to the reaction and the reaction was continued until the NCO analyzed zero I.R. The resultant product had an OH content of 0.10 meq./g., an NCO content of 0.01 meq./g. and a C=C content of 2.79 mmoles/g. and will be referred to hereinafter as thixotropic agent H.

EXAMPLE 3

1043 g. of commercially available toluene diisocyanate and 8.8 g. of triphenyl phosphite were charged to a resin kettle equipped with heating mantle, stirrer, thermometer and addition funnel. 778.5 g. of hydroxypropyl acrylate was added dropwise while maintaining the temperature between 60°–65° C. The reaction was continued with stirring at 60°–65° C. for 7 additional hours. The resultant adduct was then added to 1165.5 g. of melted glycerol monostearate commercially available from Glycol Chemicals Inc. under the tradename "ALDO MSLG" (m. pt. 57°–61° C.) and 2.33 g of stannous octoate. The reaction was continued with stirring at 65° C. for 8 hours at which time the NCO content was substantially 0 meq./g. The resultant product will hereinafter be referred to as thixotropic agent J.

The following examples show the preparation of a U.V. curable overprint varnish containing a thixotropic agent of the instant invention.

EXAMPLE 4

46.8 g. of toluene diisocyanate and 2.0 g. of triphenyl phosphite were charged to a 1000 ml. resin kettle equipped with heating mantle, stirrer, thermometer and an addition funnel. 35.1 g. of hydroxypropyl acrylate was added dropwise while maintaining the temperature at about 60° C. The reaction was continued with stirring at 60° C. for 2 hours after the addition of the hydroxypropyl acrylate. 11.0 g. of commercially available glycerol monostearate was added to the reaction with stirring at 60° C. The reaction was cooled to 45° C. and 134.0 g. of commercially available polypropylene glycol having a molecular weight of about 1000 was added to the kettle along with 0.10 g. of stannous octoate as a catalyst. The reaction was continued at 60° C. for three hours at which time residual NCO was 0.02 meq./g. as measured by I.R. The resultant product containing thixotropic agent J from Example 3 was formulated into a U.V. curable overprint varnish in the following manner. 171.0 g. of trimethylolpropane triacrylate was added to the resultant product with stirring at 55° C. followed by the addition of 2.0 g. of triphenyl phosphite, 1.25 g. of ditertiary butyl phenol, 20.0 g. benzophenone, 4.0 g. 2,2-dimethoxy-2-phenylacetophenone, 2.0 g. powdered polyethylene, and 72.0 g. of pentaerythritol tetrakis(3-mercaptopropionate). The mixture was stirred at 55° C. for 2½ hours. The resultant U.V. curable overprint varnish was creamy white with a viscosity in the range 4000–5000 centipoises as determined on a Brookfield Viscometer at 60 rpm. using a #4 spindle.

EXAMPLE 5

355 lbs. of toluene diisocyanate was charged to a 300 gallon stainless steel reactor and the temperature held at 120° F. A total of 395 lbs. of trimethylolpropane diallyl ether was added at a rate such that the temperature did not exceed 140° F. When all the trimethylolpropane diallyl ether was added heat was put on reactor to hold temperature at 140° F. until NCO dropped to ~2.5 meq./q. 226 g. of stannous octoate was then added and temperature raised to 150° F. 100 lbs. of glycerol monostearate, which had been heated in an oven at 220° F. to melt it, was then added slowly at a rate such that temperature was held at 170° F. 181 lbs. of di(2-hydroxyethyl)dimethylhydantoin was then added and temperature was allowed to go to 210° F. When all di(2-hydroxymethyl)dimethylhydantoin was charged temperature was held at 215° F. until NCO dropped to <0.01 meq./g. 246 g. of H$_3$PO$_3$, 123 g. of pyrogallol and 627 g. of hydroquinone were then charged to the reactor. After mixing 30 minutes at 200° F., 576 lbs. of trimethylolpropane tris(3-mercaptopropionate) was added. Cooling water was put on the reactor to bring the temperature to 130° F. Then 1165 lbs. of trimethylolpropane triacrylate, 21 lbs. of powdered polyethylene, 134 lbs. of benzophenone, and 90 lbs. of benzoin isopropyl ether were charged. The ingredients were mixed for 4 hours at 130° F. After degassing 1 hour the U.V. curable overprint varnish product was discharged. The resultant U.V. curable overprint varnish had a viscosity in the range 3000–4000 centipoises as determined on a Brookfield Viscometer at 60 rpm. using a #4 spindle.

EXAMPLE 6

Sheets of clay-coated SPS paperboard 58" by 48" were fed to a Harris 6 color 16" offset press containing 5 colors of U.V. curable inks in the ink units. Following the ink unit, the varnish unit was charged with the composition of Example 14. The high viscosity varnish was charged to the last press unit which transferred the varnish through forming rollers at which point the formulation shearthins to a lower viscosity, readily applicable varnish which wet-traps the U.V. inks. The sheets, after passing through the U.V. ink stations and the varnish station, were passed under 5 U.V. lamps, 60" in length, delivering an output intensity of 200 watts per inch onto the coated paperboard passing at a speed of 7000 impressions per hour. This simultaneously completely cured both the inks and varnish. The overvarnish was applied at a rate of 1 lb. per 4000 sq. ft. or approximately 0.1–0.2 ml. thickness. The resultant inked and overvarnished paperboard showed a hard, glossy, cured, scuff-resistant finish which is then converted into folding cartons using conventional equipment.

EXAMPLE 7

Example 4 was repeated except that the glycerol monostearate was omitted and replaced by an equivalent amount, based on hydroxyl content, of polypropylene glycol. A varnish was thus attained that contained no thixotropic agent.

Both this material and that from Example 4 were used as a varnish over a standard GATF test image printed down with Sinclair or Valentine black UV ink on polycoated carton board. A Miller TP-38 Defector Offset Press equipped with an Inmont 2-lamp UV oven was used. The varnish from Example 4 containing the thixotropic agent coated without misting and gave a smooth glossy appearance. The material of the present example in which the thixotropic agent was absent misted severely on press and gave a coating that had a non-smooth, textured appearance.

The following example shows the use of the thixotropic agent in wet trapping a conventional solvent based ink.

EXAMPLE 8

A typical container cardboard was printed with a conventional air-drying ink. The ink did not contain the waxy materials normally included for gloss. The ink was applied with a "Quick Peek Color Proofing Kit". A measured amount of ink was distributed evenly on a block with a roller and part of it was transferred with the roller to the board. Immediately following, the still wet ink was trapped with a layer of the material from Example 4, using the same application technique as that used for the ink. The printed and coated board was then passed at 100 ft/minute under one 200 w/inch mercury lamp placed perpendicular to the direction of travel of the board and at a distance of about 6" from the board. Following photocure, the surface was nontacky although the ink under the coating remained wet. When several layers of such printed and coated boards were placed on top of one another and a weight was applied, equal to the weight of a 4 ft high stack of boards, there was no adhesion between the boards. Further tests were conducted on the board after allowing several days for the drying of the ink through oxidation. The gloss, measured with a Gardner Glossmeter with a 75° head, was 64% and, when a surfactant DC190 (Dow-Corning silicone) was added to the material of Example 4 at a concentration of 0.5% by weight, the gloss was improved to 75%. On a rub resistance test the coating showed only slight wear and the adhesion, tested with pressure sensitive tape applied to and removed from a crosshatched area, was satisfactory. The coating weight of the overprint varnish was determined by weighing to 0.5 lb per 1000 sq. ft.

The following example shows the use of a UV curable overprint varnish containing a thixotropic agent of the instant invention to overprint a previously dried ink.

EXAMPLE 9

Previously printed dried sheets of paperboard were fed to a Mehle offset press. One unit of this press was charged with the composition of Example 4. The sheets after being varnished were passed under three 200 w/inch UV lamps. The resulting varnished boards showed a hard, glossy abrasion resistant surface.

We claim:

1. A radiation curable thixotropic agent containing terminal ethylenic unsaturation of the formula:

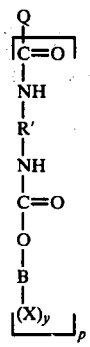

wherein
Q is the residue obtained by removal of H from primary OH groups of the reaction product from the esterification of a polyhydric alcohol containing primary OH groups with only a fatty carboxylic acid containing 4 to 26 carbon atoms in a saturated aliphatic hydrocarbon chain;

R' is an aliphatic or aromatic polyvalent organic moiety of a polyisocyanate after reaction of the isocyanato groups;

B is an aliphatic hydrocarbon containing 1–36 carbon atoms;

X is a member of the group consisting of $-OCH_2CH=CH_2$ $-CH=CH_2$ and

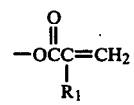

wherein $R_1$ is hydrogen or a methyl group and p and y are each integers from 1–10.

2. A composition comprising a liquid curable vehicle and about 5–15% by weight of the composition of a radiation curable thixotropic agent containing terminal ethylenic unsaturation of the formula:

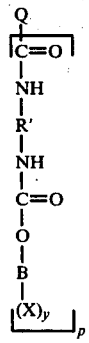

wherein
Q is the residue obtained by removal of H from primary OH groups of the reaction product from the esterification of a polyhydric alcohol containing primary OH groups with only a fatty carboxylic acid containing 4 to 26 carbon atoms in a saturated aliphatic hydrocarbon chain;

R' is an aliphatic or aromatic polyvalent organic moiety of a polyisocyanate after reaction of the isocyanato groups;

B is an aliphatic hydrocarbon containing 1-36 carbon atoms;

X is a member of the group consisting of

—OCH$_2$CH=CH$_2$

—CH=CH$_2$ and

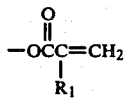

wherein R$_1$ is hydrogen or a methyl group and p and y are each integers from 1-10.

3. The composition of claim 2 wherein the liquid curable vehicle is about 98 to 2 percent by weight of a liquid polyene containing at least 2 reactive unsaturated carbon to carbon bonds per molecule and about 2 to 98 percent by weight of a polythiol containing at least 2 thiol groups per molecule, the total combined functionality of (a) the reactive terminal unsaturated carbon to carbon bonds per molecule in the polyene and (b) the thiol groups per molecule in the polythiol being greater than 4.

4. The composition of claim 3 including 1-20% by weight of a photosensitizer.

5. The composition of claim 2 wherein the liquid curable vehicle is an ethylenically unsaturated monomer.

6. The composition of claim 5 wherein the ethylenically unsaturated monomer is a member of a group consisting of acrylates, triacrylates, methacrylates, dimethacrylates, trimethacrylates and mixtures thereof.

7. The process of forming a varnished printed paper product which comprises feeding the paper product to a color offset press, applying at least one UV curable colored ink in the desired design to a surface of the paper product, wet trapping the applied ink with a UV curable overprint varnish composition comprising a liquid photocurable vehicle and about 5-15% by weight of the vehicle of a radiation curable thixotropic agent containing terminal ethylenic unsaturation of the general formula:

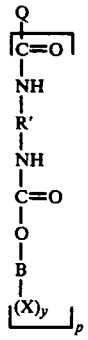

wherein

Q is the residue obtained by removal of H from primary OH groups of the reaction product from esterification of a polyhydric alcohol containing primary OH groups with only a fatty carboxylic acid containing 4 to 26 carbon atoms in a saturated aliphatic hydrocarbon chain;

R' is an aliphatic or aromatic polyvalent organic moiety of a polyisocyanate after reaction of the isocyanate groups, B is an aliphatic hydrocarbon containing 1-36 carbon atoms, X is a member of the group consisting of

—OCH$_2$CH=CH$_2$

—CH=CH$_2$ and

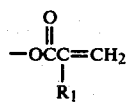

wherein R$_1$ is hydrogen or a methyl group and p and y are each integers from 1-10 and, thereafter, exposing the overprint varnish and ink to UV radiation for a time sufficient to simultaneously cure the ink and varnish thereby forming a glossy, hard, cured coating on the printed surface.

8. The process of forming a varnished printed paper product which comprises feeding the paper product to a color offset press, applying at least one conventional solvent based colored ink in the desired design to a surface of the paper product, wet trapping the applied ink with a UV curable overprint varnish composition comprising a liquid photocurable vehicle and about 5-15% by weight of the vehicle of a radiation curable thixotropic agent containing terminal ethylenic unsaturation of the general formula:

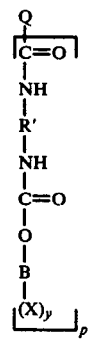

wherein

Q is the residue obtained by removal of H from primary OH groups of the reaction product from the esterification of a polyhydric alcohol containing primary OH groups with only a fatty carboxylic acid containing 4 to 26 carbon atoms in a saturated aliphatic hydrocarbon chain;

R' is an aliphatic or aromatic polyvalent organic moiety of a polyisocyanate after reaction of the isocyanate groups, B is an aliphatic hydrocarbon containing 1–36 carbon atoms, X is a member of the group consisting of

—OCH₂CH=CH₂

—CH=CH₂ and

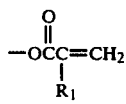

wherein R₁ is hydrogen or a methyl group and p and y are each integers from 1–10 and, thereafter, exposing the overprint varnish composition to UV radiation for a time sufficient to form a glossy, hard, cured coating on the printed paper product.

9. The process of forming a varnished paper product which comprises applying to the surface of said paper product a U.V. curable varnish composition comprising a liquid photocurable vehicle and about 5–15% by weight of the vehicle of a radiation curable thixotropic agent containing terminal ethylenic unsaturation of the general formula:

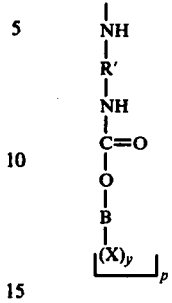

wherein
Q is the residue obtained by removal of H from primary OH groups of the reaction product from the esterification of a polyhydric alcohol containing primary OH groups with only a fatty carboxylic acid containing 4 to 26 carbon atoms in a saturated aliphatic hydrocarbon chain;
R' is an aliphatic or aromatic polyvalent organic moiety of a polyisocyanate after reaction of the isocyanate groups,
B is an aliphatic hydrocarbon containing 1–36 carbon atoms,
X is a member of the group consisting of

—OCH₂CH=CH₂

—CH=CH₂ and

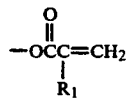

wherein R₁ is hydrogen or a methyl group and p and y are each integers from 1–10 and, thereafter, exposing the varnish to UV radiation for a time sufficient to cure the varnish thereby forming a glossy, hard, cured coating on the surface.

10. The process according to claim 9 wherein the surface of the paper product has printing ink thereon prior to the application of the UV curable varnish.

* * * * *